(12) United States Patent
Tsvetkova et al.

(10) Patent No.: US 8,187,799 B2
(45) Date of Patent: May 29, 2012

(54) STABILIZATION OF LIQUID SOLUTIONS OF RECOMBINANT PROTEIN FOR FROZEN STORAGE

(75) Inventors: Nelly Tsvetkova, Vallejo, CA (US); Omkar Joshi, Albany, CA (US); Paul Wu, Orinda, CA (US); Deqian Wang, Concord, CA (US); Arnaud Desponds, Yverdon-les-Bains (CH)

(73) Assignee: Bayer HealthCare LLC, Tarrytown, NY (US)

( * ) Notice: Subject to any disclaimer, the term of this patent is extended or adjusted under 35 U.S.C. 154(b) by 8 days.

(21) Appl. No.: 12/597,333

(22) PCT Filed: Apr. 22, 2008

(86) PCT No.: PCT/US2008/061147
§ 371 (c)(1),
(2), (4) Date: Oct. 23, 2009

(87) PCT Pub. No.: WO2008/134310
PCT Pub. Date: Nov. 6, 2008

(65) Prior Publication Data
US 2010/0113744 A1    May 6, 2010

Related U.S. Application Data

(60) Provisional application No. 60/926,698, filed on Apr. 26, 2007.

(51) Int. Cl.
*A01N 1/00* (2006.01)
(52) U.S. Cl. ........................................................ 435/1.3
(58) Field of Classification Search .................. None
See application file for complete search history.

(56) References Cited

U.S. PATENT DOCUMENTS

| | | | |
|---|---|---|---|
| 4,457,916 | A | 7/1984 | Hayashi et al. |
| 4,877,608 | A | 10/1989 | Lee et al. |
| 5,278,289 | A | 1/1994 | Johnson et al. |
| 5,565,427 | A | 10/1996 | Freudenberg |
| 5,576,194 | A | 11/1996 | Chan |
| 5,576,291 | A | 11/1996 | Curtis et al. |
| 5,605,884 | A | 2/1997 | Lee et al. |
| 5,733,873 | A | 3/1998 | Osterberg et al. |
| 5,763,401 | A | 6/1998 | Nayar |
| 5,804,420 | A | 9/1998 | Chan et al. |
| 5,919,766 | A | 7/1999 | Osterberg et al. |
| 5,925,739 | A | 7/1999 | Spira et al. |
| 6,100,061 | A | 8/2000 | Reiter et al. |
| 6,790,439 | B1 | 9/2004 | Senderoff et al. |
| 7,033,992 | B2 | 4/2006 | Warne et al. |
| 7,087,723 | B2 | 8/2006 | Besman et al. |
| 2004/0116345 | A1 | 6/2004 | Besman et al. |
| 2004/0248778 | A1 | 12/2004 | Gloger et al. |
| 2004/0248793 | A1 | 12/2004 | Jensen et al. |
| 2006/0205661 | A1 | 9/2006 | Besman et al. |

FOREIGN PATENT DOCUMENTS

| | | |
|---|---|---|
| EP | 0 117 064 A2 | 8/1984 |
| WO | WO-9726909 A1 | 7/1997 |
| WO | WO-2005014025 A1 | 2/2005 |

OTHER PUBLICATIONS

Suck, K., et al., "Fast and Efficient Protein Purification Using Membrane Adsorber Systems", J. Biotechnol, Feb. 10, 2006, vol. 121(3) 361-7. (Abstract).

*Primary Examiner* — Suzanne M Noakes
*Assistant Examiner* — Jae W Lee
(74) *Attorney, Agent, or Firm* — Connolly Bove Lodge & Hutz LLP

(57) ABSTRACT

The invention relates to a method for stabilizing a bulk solution of recombinant protein for frozen storage, which comprises providing a partially-purified solution of recombinant protein which has a monovalent salt concentration of at least 100 mM, and adding a carbohydrate to said solution in an amount sufficient that, upon freezing, the solution has a glass transition temperature of −56° C. or higher.

18 Claims, 2 Drawing Sheets

STABILIZATION OF LIQUID SOLUTIONS OF RECOMBINANT PROTEIN FOR FROZEN STORAGE

This application claims benefit of Provisional Patent application 60/926,698, filed Apr. 26, 2007, the disclosure of which is incorporated by reference.

FIELD OF THE INVENTION

The invention relates to the freezing and storage of liquid solutions of recombinant protein, preferably bulk solutions.

BACKGROUND OF THE INVENTION

Production of recombinant proteins in cell culture normally involves a series of purification steps, by which the desired protein product is recovered from recombinant host cells and/or the associated culture media. Many important recombinant proteins are produced on a large commercial scale. In the case of pharmaceutical proteins, for example, it is not uncommon for more than one purification stage to be used to achieve the desired level of product purity.

It can be necessary to store a bulk solution of recombinant protein which has been initially purified, but not finally purified, prior to final purification for formulation. For example, a protein-containing product of a recombinant fermentation reaction can be initially purified in an affinity or ion exchange column. After an initial pass through the column, the protein product is only partially purified, and the solution still contains contaminants such as remnants of the cell culture and other proteins. Prior to final formulation into a pharmaceutical product, the bulk solution must be further processed to obtain the protein in a satisfactory purity.

Normally the solution, e.g. elution buffer, which is used to recover the protein from a first-pass purification treatment is a high salt solution. In the case of elution from a column, a high salt concentration is needed to release the protein from the column. Accordingly, the "bulk" solution recovered from first pass purification treatment can comprise a solution having a high concentration of monovalent salts, normally sodium chloride but potentially potassium chloride, or other salts.

The storage of a "bulk" solution of recombinant protein poses unique challenges due to the high salt concentration and very low protein concentration of the solution. Ideally, proteins are stored below the glass transition temperature to assure stability, since in the glassy state, protein inactivation and denaturation are extremely slow on a pharmaceutical time scale. On the other hand, the presence of high salt concentration in a solution tends to depress its glass transition temperature, and in solutions with high salt concentration and low protein concentration, very low temperatures are needed to achieve this state.

Frozen storage at higher temperature is desirable for bulk solutions in large volume quantities for cost and efficiency reasons, but while preserving the stability and activity of the protein.

SUMMARY OF THE INVENTION

The invention is a method for stabilizing a liquid solution of recombinant protein for frozen storage, which comprises: providing a solution of recombinant protein wherein said solution has a monovalent salt concentration, e.g. of NaCl and/or KCl, of at least 100 mM; adding a carbohydrate to said solution in an amount sufficient to provide the solution, upon freezing, with a glass transition temperature of −56 C. or higher; and freezing said solution for storage.

The invention also provides a liquid solution of recombinant protein which is stabilized for frozen storage, which contains a carbohydrate in an amount sufficient to provide the solution, upon freezing, with a glass transition temperature of −56 C. or higher

DESCRIPTION OF PREFERRED EMBODIMENTS

Figure 1:
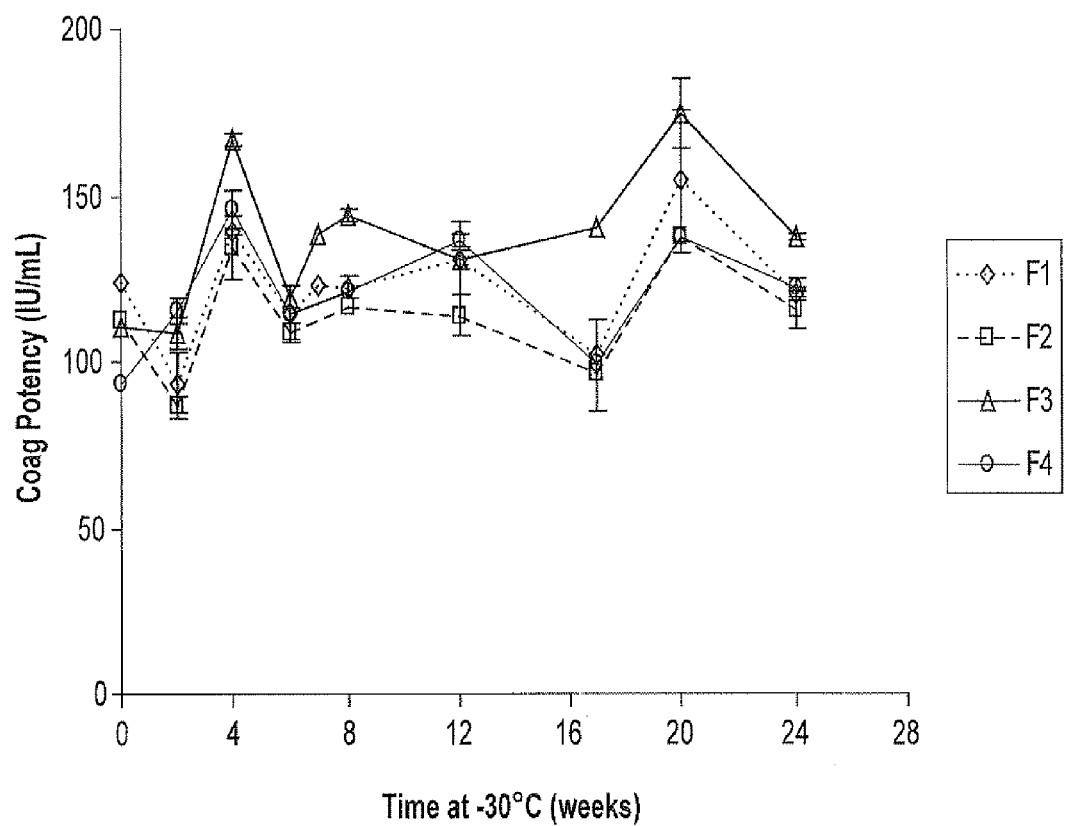
FIG. 1 shows the effect on preserving recombinant protein activity of adding carbohydrate, with or without other excipients as described in the text, to a bulk solution of recombinant Factor VIII. The four different formulations are designated F1, F2, F3 and F4. Factor VIII activity was assayed after freezing and storage at −30° C., at different time points as shown, for up for 24 weeks. Before addition of carbohydrate, the bulk solution contained approximately 600 mM NaCl, 10 mM $CaCl_2$, 20 mM imidazole and 0.1% Triton X-100, except F3 which was diluted as described herein. The graph plots time against coagulation potency (IU/mL).

The liquid solution of recombinant protein may comprise a solution of any recombinant protein obtained from recombinant cell culture using affinity chromatography, ion-exchange chromatography, or the like. In a preferred embodiment, the solution is a bulk solution, which comprises a solution which has been partially purified. In all embodiments, the liquid solution is a high-salt solution, preferably an aqueous solution.

Recombinant proteins include, for example and without limitation, coagulation factors, virus antigens, bacterial antigens, fungal antigens, protozoal antigens, peptide hormones, chemokines, cytokines, growth factors, enzymes, blood proteins such as hemoglobin, α-1-antitrypsin, fibrinogen, human serum albumin, prothrombin/thrombin, antibodies, blood coagulation and/or clotting factors, and biologically active fragments thereof; such as Factor V, Factor VI, Factor VII, Factor VIII and derivatives thereof such as B-domain deleted FVIII, Factor IX, Factor X, Factor XI, Factor XII, Factor XIII, Fletcher Factor, Fitzgerald Factor, and von Willebrand Factor; milk proteins such as casein, lactoferrin, lysozyme, α-1 anti-trypsin, protein factors, immune proteins, and biologically active fragments thereof; and antibodies, including monoclonal antibodies, single chain antibodies, antibody fragments, chimeric antibodies, humanized antibodies, and other antibody variant molecules which can be produced in recombinant cell culture.

A currently preferred recombinant protein is recombinant Factor VIII. Factor VIII as used herein includes engineered variants of Factor VIII, such as B-domain deleted variants of Factor VIII.

A "bulk" solution within the meaning of the present invention comprises a partially but not fully purified liquid solution of recombinant protein, which contains at least 100 mM monovalent salt. The monovalent salt is preferably NaCl which is commonly used to elute recombinant proteins from purification columns. However, the NaCl may be replaced, in whole or in part, with KCl. The bulk solution may also contain varying amounts of other salts, such as divalent salts including calcium chloride.

By "partially but not fully purified" is meant the liquid solution has been subjected to at least one purification step, but the liquid solution still contains sufficient residual impurities that at least one further purification step is required prior to final product formulation. For example, a "bulk" solution of recombinant Factor VIII must be further purified prior to final formulation, which in the case of Factor VIII and other proteins may include lyophilization.

The liquid solution contains at least 100 mM monovalent salt, preferably 100 mM NaCl, more preferably at least 300 mM NaCl, more preferably at least 500 mM NaCl, more preferably at least 560 mM NaCl and still more preferably at least 600 mM NaCl. It is not uncommon for bulk solutions of recombinant protein to have this high monovalent salt concentration following an initial purification stage.

In further embodiments of the invention, the liquid solution contains 100-200 mM NaCl, 100-300 mM NaCl, 200-300 mM NaCl, 100-400 mM NaCl, 100-500 mM NaCl, 100-600 mM NaCl, 100-800 mM NaCl, 300-500 mM NaCl, 300-600 mM NaCl 300-800 mM NaCl, 400-600 mM NaCl, 400-800 mM NaCl, 500-600 mM NaCl, 560-700 mM NaCl and 500-800 mM NaCl.

The "bulk" solutions of the invention are further characterized by their very low protein concentration. In embodiments of the invention, the concentration of recombinant protein in the bulk solution can be as low as 0.0001 micromolar, 0.001 micromolar, or 0.01 micromolar. In embodiments of the invention, the concentration of recombinant protein in the bulk solution can be as high as 10 micromolar, 1 micromolar, or 0.1 micromolar. Any concentration of protein falling within any combination of these upper and lower limits is an embodiment of a "bulk" solution within the meaning of the invention.

The carbohydrate is added to the liquid solution, prior to freezing, in an amount sufficient to provide the solution, upon freezing, with a glass transition temperature of −56° C. or higher, more preferably at least −34° C., or any temperature expressed by a whole or fractional number therebetween. The normal glass transition temperature of a high salt, low protein bulk solution is substantially less than −56° C., e.g. −60 to −70° C. The amount of added carbohydrate needed to elevate the glass transition temperature to −56° C. should take into account, as one factor, the protein concentration. Higher protein concentrations tend to themselves elevate the glass transition temperature of a bulk solution. As other factors, the amount of carbohydrate should not excessively increase the viscosity of the solution, and preferably the viscosity is maintained below about 9.0 cP. The conductance of the solution can be changed by carbohydrate addition, and preferably, should be maintained below about 39 mS/cm.

Freezing the solution, in the context of the present invention, means freezing the bulk liquid solution, and is to be distinguished from freeze-drying, which involves different technical considerations.

The carbohydrate can be the type of carbohydrate normally used in pharmaceutical formulations, including sugars and di-, oligo- and poly-saccharides. Examples include dextrans, cyclodextrans, chitosans, starches, halyuronic acids, cellulose, raffinose, maltose, lactose, stachyose, and combinations thereof. Preferred examples are carbohydrates which are approved for injection, which includes sucrose, trehalose, hydroxyethylstarch, dextran, or combinations thereof. Pharmaceutical grade carbohydrates are available commercially from a number of suppliers.

The precise amount of carbohydrate needed to protect the solution during freezing can be readily determined, for example by differential scanning calorimetry, and depends on the particular protein and the particular carbohydrate. Currently preferred amounts of carbohydrate are 8-25% (w/w) based on weight of liquid solution.

In specific embodiments of the invention, the amounts of carbohydrate are about 8-15%, 12-20%, 16-20%, 15-25%, and 20-25% (w/w) based on weight of liquid solution.

Other components from the initial purification (e.g. elution) may be present in a bulk solution, including a surfactant (e.g. Tween 80 or Triton-X), calcium chloride, or imidazole. Other excipients can be added to the liquid solutions. As shown in the below formulations, additional surfactant may be added as an excipient. As a further excipient, an amino acid (e.g. glycine) may be added.

EXAMPLES

The invention is illustrated using, as exemplary recombinant protein, recombinant Factor VIII. Recombinant Factor VIII is produced using methods known in the art, for example as described in U.S. Pat. Nos. 5,576,194; 5,804,420; and 5,733,873. In preferred embodiments, recombinant Factor VIII is produced in mammalian cells in large-scale fermentation reactors, in media which can be serum-free and/or protein free. Preferably the recombinant Factor VIII is secreted into the media by the recombinant cells.

Recombinant Factor VIII (full length) was expressed from host cells and purified from clarified tissue culture fluid by membrane adsorber chromatography. The membrane adsorber process isolates and concentrates recombinant Factor VIII from the tissue culture fluid by binding and elution (generally as described in Suck et al., J. Biotechnology, 121: 361-367, 2006.) The eluate was divided into four batches and each batch was transferred into a sterile bottle (400 mL in each bottle). In addition to recombinant Factor VIII and residual impurities which remain, the eluate (bulk solution) contained approximately 600 mM NaCl, 10 mM $CaCl_2$, 20 mM imidazole and 0.1% Triton X-100. The concentration of recombinant Factor VIII in the eluate was approximately 0.067 micromolar.

A carbohydrate or combination of carbohydrates, along with other excipients as indicated, were then added to each bottle at room temperature in the amounts shown as Formulations 1, 2, 3 and 4 in Table 1 below.

TABLE 1

| Formulation 1 | Formulation 2 | Formulation 3 | Formulation 4 |
|---|---|---|---|
| 8% Sucrose<br>3% Glycine | 15% Sucrose | 10% Hydroxyethyl starch<br>8% Trehalose<br>80 ppm Tween | 15% Dextran<br>8% Trehalose<br>80 ppm Tween |

All components in Table 1 are shown in percent by weight based on weight of solution. Carbohydrates and other excipients were obtained commercially. Each fresh formulated batch was sampled. Samples from Formulations (1), (2), (3) and (4) were assessed for Factor VIII activity using a standard coagulation assay.

Formulation 3 was prepared from the same eluate but was diluted with a buffer containing 20 mM imidazole and 10 mM CaCl$_2$ to decrease the NaCl concentration by half. This dilution was performed to examine the applicability of the process of the invention to solution having a lower, but still relatively high, monovalent salt concentration.

The glass transition temperature of each sample was determined using Differential Scanning Calorimetry (DuPont Modulated DSC). The glass transition temperatures exhibited by Formulations 1, 2, 3 and 4 were, respectively, −56° C., −52.1° C., −34.9° C. and −35.5° C. In each case, the glass transition temperature is significantly higher than the glass transition temperature observed in the absence of an added carbohydrate (which for the same bulk solution without carbohydrate was determined to be between −60 and −70° C.). The viscosities of the formulations were: Formulation 1: 1.8428 cP; Formulation 2: 3.1089 cP; Formulation 3: 6.8076 cP; and Formulation 4: 7.2123 cP. The conductivities of the formulations were: Formulation 1: 27.8 mS/cm; Formulation 2: 25.57 mS/cm; Formulation 3: 21.05 mS/cm; and Formulation 4: 32.1 mS/cm.

All of the formulations were found to be stable after frozen storage at −80, −30 −18 and −14° C. up to 24 weeks, as determined by coagulation assay for Factor VIII activity at various time points, without significant loss of activity.

As shown in FIG. 1, all four formulations in accordance with the invention maintained Factor VIII coagulation activity at substantially the initial level after storage at −30° C. for up to 24 weeks.

Figure 2:
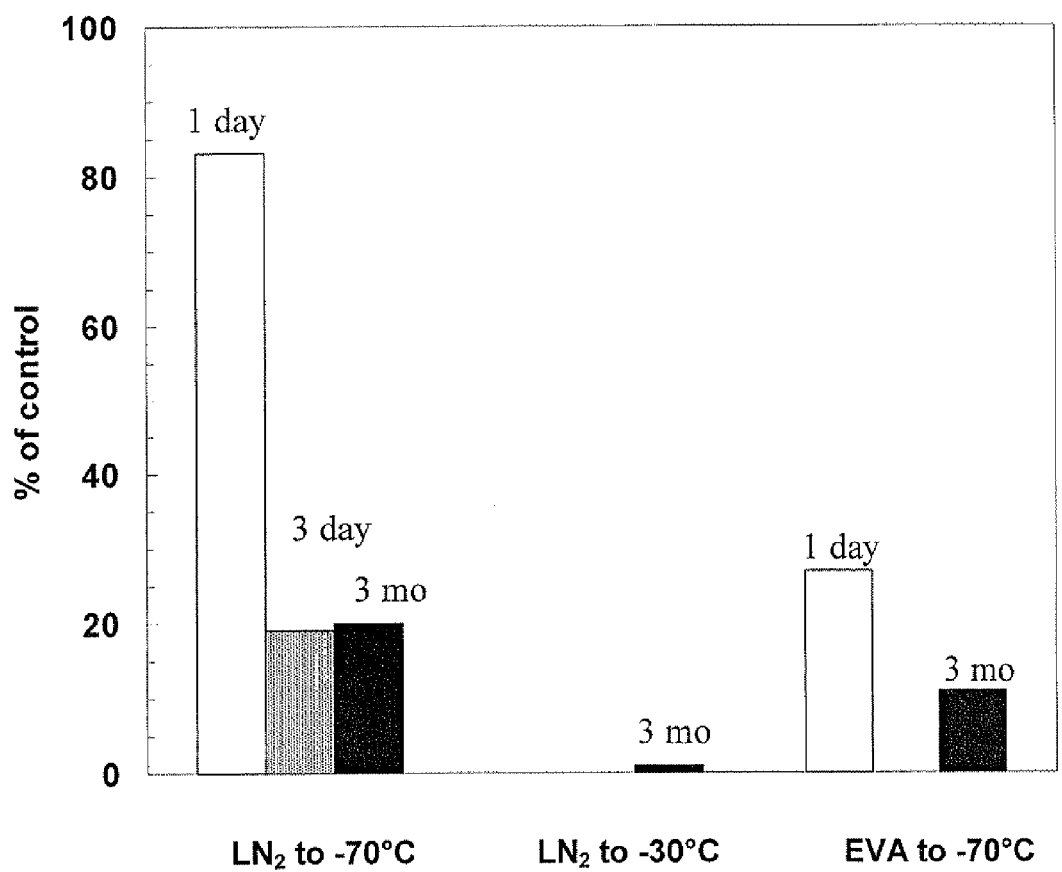
FIG. 2 shows loss of recombinant FVIII activity after freezing and storage at −70° C. and −30° C. of the bulk Factor VIII solution used in the experiments illustrated in FIG. 1 but without stabilization excipients. The designation "$LN_2$ to −70° C." indicates that the samples were frozen in liquid nitrogen prior to storage at −70° C., and "$LN_2$ to −30° C." indicates that the samples were frozen in liquid nitrogen prior to storage at −30° C. "EVA to −70° C." indicates that the samples were frozen in polymer storage bags and stored at −70° C.

As shown in FIG. 2, in the absence of the added excipients, the solution lost substantially all of its Factor VIII coagulation activity after only 1 day of storage at −30° C.

What is claimed is:

1. A method for stabilizing a liquid solution of coagulation and/or clotting factors for frozen storage, which comprises:
   a. providing a liquid solution of coagulation and/or clotting factors wherein said solution has an NaCl and/or KCl concentration of at least 100 mM;
   b. adding a carbohydrate to said solution in an amount sufficient to provide the solution, upon freezing, with a glass transition temperature of −56° C. or higher;
   c. freezing said solution; and
   d. storing said solution at temperatures under which said solution is frozen without freeze-drying said solution wherein after freezing said solution for up to 24 weeks, said coagulation and/or clotting factors substantially maintain the initial level of coagulation activity present prior to freezing.

2. The method as claimed in claim 1, wherein the liquid solution of coagulation and/or clotting factors is a bulk solution.

3. The method as claimed in claim 1, wherein the solution has an NaCl concentration of at least 100 mM.

4. The method as claimed in claim 1, wherein the carbohydrate is added in an amount of 8-25% by weight, based on weight of solution.

5. The method as claimed in claim 1, wherein the carbohydrate is selected from the group consisting of sucrose, trehalose, hydroxyethylstarch, dextran, and combinations thereof.

6. The method as claimed in claim 2, wherein the bulk solution has an NaCl concentration of at least 300 mM.

7. The method as claimed in claim 2, wherein the bulk solution has an NaCl concentration of at least 600 mU.

8. The method as claimed in claim 1, wherein the coagulation and/or clotting factors is Factor VIII or a derivative thereof.

9. The method as claimed in claim 1, wherein the glass transition temperature is between −56° C. and −35° C.

10. The method as claimed in claim 1, further comprising adding an amino acid and/or a surfactant to the solution before freezing.

11. A method for preparing a pharmaceutical formulation of a coagulation and/or clotting factors, which method comprises:
    a. providing a bulk liquid solution of the coagulation and/or clotting factors wherein said bulk liquid solution has an NaCl and/or KCl concentration of at least 100 mM;
    b. adding a carbohydrate to said bulk liquid solution in an amount sufficient to provide said bulk liquid solution, upon freezing, with a glass transition temperature of −56° C. or higher;
    c. freezing said solution;
    d. storing said solution at temperatures under which said solution is frozen without freeze-drying said solution wherein after freezing said solution for up to 24 weeks, said coagulation and/or clotting factors substantially maintain the initial level of coagulation activity present prior to freezing;
    e. thawing said solution;
    f. purifying said solution to obtain a purified solution of the coagulation and/or clotting factors and
    g. formulating the coagulation and/or clotting factors obtained from the purified solution into a pharmaceutical formulation.

12. The method as claimed in claim 11, wherein the carbohydrate is added in an amount of 8-25% by weight, based on weight of said bulk liquid solution.

13. The method as claimed in claim 11, wherein the carbohydrate is selected from the group consisting of sucrose, trehalose, hydroxyethylstarch, dextran, and combinations thereof.

14. The method as claimed in claim 11, wherein the bulk liquid solution has an NaCl concentration of at least 300 mM.

15. The method as claimed in claim 11, wherein the bulk liquid solution has an NaCl concentration of at least 600 mU.

16. The method as claimed in claim 11, wherein the coagulation and/or clotting factors is Factor VIII or a derivative thereof.

17. The method as claimed in claim 11, wherein the glass transition temperature is between −56° C. and −35° C.

18. The method as claimed in claim 11, further comprising adding an amino acid and/or a surfactant to the bulk liquid solution before freezing.

* * * * *